United States Patent [19]

Cohen

[11] 4,148,303

[45] Apr. 10, 1979

[54] METHOD OF ASSESSING INTENTIONAL MUSCULAR DISABILITY

[76] Inventor: Leonard A. Cohen, 15951 Harden Cir., Southfield, Mich. 48075

[21] Appl. No.: 721,845

[22] Filed: Sep. 9, 1976

[51] Int. Cl.² .............................................. A61B 5/05
[52] U.S. Cl. ................................ 128/2 R; 128/2.1 M
[58] Field of Search ................................... 128/2.1 M

[56] References Cited

U.S. PATENT DOCUMENTS

| | | | |
|---|---|---|---|
| 3,905,355 | 9/1975 | Brudny | 128/2.1 M |
| 3,916,876 | 10/1975 | Freeman | 128/2.1 M |

FOREIGN PATENT DOCUMENTS 1504205  10/1967  France ................................. 128/2.1 M

OTHER PUBLICATIONS

Garland et al., "Tech. Note: State Variable Filter for EMG Processing," Med. & Biol. Eng., V 10, pp. 559-560, 1972.

"Clinical Manifestations of Muscle Disease," Chapter 343, Harrison's *Principles of Internal Medicine*, McGraw-Hill, 1974, pp. 1905-1910.

"Physiology" by *Guyton*, W. B. Saunders Co., 1974, pp. 650-651.

"Essentials of the Neurologic Examination"—Alpers & Mancall, F.A. Davis Co., Philadelphia, 1971, pp. 66-71.

"The Peripheral Nervous System and Electromyography," in Medical Engineering by C. Ray, Yearbook Publishers Chicago, 1974, p. 457.

"EMG and Electrodiagnosis in Invalidness Assessment," Sommella & Serra, Electromyography, vol. 9, Nov.-Dec. 1969, pp. 433-445.

"Method of Evaluation of Muscle Fatigue Curves," De Vries, H. A., Amer. Jrnl. of Physical Medicine, V. 47, Jun. 1968, pp. 125-135.

"EMG Evaluation of Nerve Injuries in Hospitalized Patients"—Marinacci, A. A., Electromyography, vol. 6, Aug.-Oct. 1966.

"Radicolopathy and the EMG in Disability Applicants"—Jebsen, R. H. et al., Archives of Physical Medicine & Rehabilitation, vol. 54, Oct. 1973, pp. 471-474.

"EMG Feedback Therapy: review of 114 patients" Brudny, J. et al., Archives of Phys. Med. & Rehab., vol. 57 #2, Feb. 1976, pp. 55-61.

"EMG Evaluation of Patients w/Post-Traumatic Cervical Pain," Reynolds, G. C. et al., Archives of Phys. Med., vol. 49, Mar. 1968, pp. 170-172.

*Primary Examiner*—Robert W. Michell
*Assistant Examiner*—Francis J. Jaworski
*Attorney, Agent, or Firm*—Cushman, Darby & Cushman

[57] ABSTRACT

A method is disclosed for detecting the intentional disabling of muscles which includes the steps of measuring the neuromuscular activation in a disabled muscle and comparing the neuromuscular activation of the muscle with that of a control muscle when performing a specified work task. To perform this comparison, an integrated electromyogram (emg) of a muscle which is synergist to the disabled muscle is compared with the integrated emg of a synergist control muscle wherein the control muscle corresponds to the disabled muscle but is on the opposite side of the human body or is the same muscle in a control population. Where only one muscle of a given type exists, the integrated emg thereof is compared with the norm of a matched population when performing the work task.

The intentional disabling of muscles can also be detected by measuring the neuromuscular activation of a muscle which is antagonist to a disabled muscle and comparing this neuromuscular activation with that of a control muscle wherein the control muscle corresponds to the antagonist of the disabled muscle but is on the opposite side of the human body or is the same muscle in a control population.

6 Claims, No Drawings

METHOD OF ASSESSING INTENTIONAL MUSCULAR DISABILITY

BACKGROUND OF THE INVENTION

This invention relates to a method and apparatus for determining whether a disabled muscle is voluntarily or involuntarily disabled.

It is becoming increasingly important in the diagnosing of disabilities to determine whether a disability is actually existing or whether it is partially or totally caused by the voluntary activity of a patient. Such an evaluation is difficult with respect to neuromuscular disabilities which constitute the largest and traditionally the most important class of disabilities, since the contraction of many muscles is under the voluntary mental control of the patient. Since, of course, one cannot readily determine whether a patient cannot or will not move a portion of his body by contracting one or more muscles, it has been next to impossible to prove whether a patient is really trying to activate and contract his muscles. Thus, for example, if a patient is claiming injury, it is difficult to determine whether his claim is truthful or is merely a malingering for the purpose of obtaining financial or other benefits.

Indirect attempts have been made to determine whether supposedly disabled muscles are in fact disabled by distracting the patient to catch him off guard during testing of the supposedly disabled muscle or by requesting repeated performance of physical movements by the patient to determine whether the claimed disability appears to be approximately the same in severity. Other attempts have been made to use surveillance to catch the patient unaware and to record the patient's body movements by photographic techniques. These methods are all indirect and require inferential determinations as to whether the alleged muscular disability in fact exists.

SHORT STATEMENT OF THE INVENTION

Accordingly, the present invention relates to a method of detecting the intentional disability of a muscle. The method includes the steps of measuring the neuromuscular activation of the disabled muscle when a predetermined movement or work task is required thereof. In addition, the neuromuscular activities of the muscles which are synergistic and antagonistic to the disabled muscle are measured while performing the aforementioned movement or work task. After these measurements are recorded, the corresponding neuromuscular activities of contralateral muscles are measured while performing the same movement or work task. The extent of purposeful disablity can thus be determined by comparing the activation of the muscle which is synergistic to the disabled muscle with the degree of activation of the synergist muscle which is contralateral thereto and by comparing the degree of activation of the antagonist muscle with respect to its contralateral muscle while performing the work task and with the degree of activation of the muscle which is contralateral to the disabled muscle. The degree of activity is measured by recording the integrated emg for each of the muscles.

DETAILED DESCRIPTION OF THE PREFERRED EMBODIMENT

In the present invention, a method and apparatus has been developed for objectively measuring the extent of malingering with respect to the neuromuscular activities of a supposedly disabled muscle. In considering the neuromuscular disability of muscles, the primary muscle is the muscle suspected of disability. In keeping with the present invention, only voluntary muscles which generate specific voluntary movements of the human body are considered. Presumably, muscles which are involuntarily activated, i.e., contracted, will not be subject to voluntary inactivation or malingering. A synergist muscle augments or supports the prime moving action of the primary muscle but does not contribute as much force to the movement as does the primary muscle. Thus, during weak contractions, only the primary muscle contracts. However, during efforts for which strong muscular contraction is required, the synergist muscles are also activated to assist the primary muscle. Such combined coordinated activity is an inevitable occurrence due to the neuroanatomical structure of the central nervous system and is a form of motor coordination. The antagonist muscle opposes the main action of the primary muscle. The primary muscle and the antagonist muscle are thus reciprocally innervated, i.e., when one of these muscles is excited, the excitement of the other is inhibited in direct proportion to the magnitude of the excitation. As an example, the biceps muscle is the prime mover for flexing the arm, while its antagonist muscle, the triceps, is the prime mover for extending the arm. The anatomical connections within the central nervous system are such that whenever the neurons to the biceps are excited sufficiently to cause the muscle to contract, the neurons to the antagonist triceps muscle which might oppose such a contraction are inhibited. In addition, during voluntary attempts to strongly contract the biceps, the synergist pronator teres muscle is simultaneously activated.

When a patient fakes a muscular disability, which often is called malingering, the disability takes one of three forms, namely, there is no contractile activity in the disabled muscle due to the patient's refusal to voluntarily activate the muscle, or there is weak muscular contraction inadequate to perform a designated task due to the patient's refusal to sufficiently activate the muscle, or there is a strong contraction in the disabled muscle but no resulting movement is achieved because the patient has simultaneously activated the antagonistic muscle by a proportional amount to thereby offset the effect of activating the disabled muscle. When no contractile activity or weak contractile activity results in an apparent disability, such can be detected and objectively measured by comparing the recorded integrated emg of the disability muscle with that of a control synergist muscle after both synergist muscles have been used in performing the same work task.

Briefly, by way of explanation, an integrated emg is the summation of all recorded voltage activity which indicates the neuromuscular activation in a muscle. The voltage activity is measured during timed intervals to thereby produce a direct measure of existing neuromuscular activity, i.e., muscle contraction. Either skin surface electrodes or needle electrodes may be used. In the preferred embodiment, a skin-strip electrode is used which stretches across most, if not all, of the surface breadth of the muscle from which a recording is to be obtained. If the muscle is deep, the strip-electrode is placed over the palpated area. This will provide a respresentative and proportional sampling of activity throughout the breadth and depth of the muscle to thereby provide a measure of the degree of contraction of the muscle. It accordingly has been found by applicant that it is unnecessary to attempt to record the voltages from all of the active fibers in a muscle and integrate these in order to obtain an accurate measure of the contractile activity in the muscle.

As is known in the art, the neuromuscular organization of the muscle is such that the active units in a muscle are quite evenly dispersed throughout the muscle regardless of the level of total muscle activity for a given specific motion. Therefore, recording and integrating voltages from a skin area across the breadth of a muscle or across the cutaneous area of palpation of a deep muscle provides an accurate measure of the activity of the muscle and the change in activity thereof throughout the range of weak to maximum voluntary contraction of the muscle.

In keeping with the method of the present invention, after an integrated emg of the disability synergist muscle and the control synergist muscle has been taken and compared, a determination as to whether the patient is really trying to contract the supposedly disabled muscle can be made. Thus, if the patient is really trying, the disability synergist muscle will show no reduction in its integrated emg with respect to the integrated emg of the control synergist muscle. Thus, the intentional disability is in proportion to the decrease in the emg of the synergist disability muscle with respect to the emg of the synergist control muscle.

If disability is evidenced by simultaneously activating the antagonist muscle when the primary muscle is activated, an objective measurement can be taken of voluntarily induced disability by calculating the increase in the integrated emg of the disability antagonist muscle over that of the control antagonist muscle while the disability primary and control primary muscles perform a similar work task.

The preferred method of applicant's invention for measuring the intentional disabling of a muscle will now be described in detail. The following equation gives an expression of the intentional disability of a muscle with respect to its related synergist muscle:

$$ID_S = 100 - 100(S_D/S_C) \tag{1}$$

where $ID_S$ is the intentional disability of a muscle with respect to its related synergist muscle, $S_D$ is the integrated emg recorded during a task performed by a muscle which is synergistic to the disabled muscle and $S_C$ is the integrated emg recorded during the same task which is performed by a contralateral muscle corresponding to the synergist muscle. For a unilateral portion of the body, such as the back or the neck, the value of $S_C$ may be derived from a norm obtained from a matched population using the same work task as the disabled patient uses. In the aforementioned equation, if the disability synergist muscle is not activated at all, the value of $S_D$ should be zero (much smaller than) and that of $S_D/S_C$ will be zero and accordingly, $ID_S$ should be approximately 100. If, on the other hand, the synergist muscle is fully activated, then $S_D$ should substantially equal $S_C$ and accordingly the value of $ID_S$ should be approximately zero. Thus, it can be seen that the intentional disabling of a muscle by refusing to activate the muscle can be determined by determining the decrease in the value of $S_D$ with respect to $S_C$.

If the patient is attempting to disable a muscle by proportionally activating his antagonist muscle, this faking of disabillity can be tested and quantized in accordance with the following equation:

$$ID_A = 100 (A_D - (A_C + A_DR))/P_C \tag{2}$$

where $ID_A$ is the measure of intentional disability with respect to the antagonist muscle, $A_D$ is the integrated emg recorded from a muscle which is antagonistic to the disabled muscle during a task performed by the disabled muscle and $A_C$ is the integrated emg recorded from the contralateral antagonist muscle during performance of the same task with the muscle which is contralateral to the disabled muscle. As in the case when measuring the intentional disability with respect to the synergistic muscle for unilateral muscles, such as in the back and neck, the value for A can be taken from a norm obtained from a matched population using the same work task as required in obtaining the measurement $A_D$. $A_DR$ is the integrated emg of the muscle antagonistic to the disability muscle when the latter is at rest and $P_C$ is the integrated emg corresponding to the contralateral primary muscle when performing the same work task. Assuming that disability is not faked, the muscle antagonistic to the disabled muscle should show no greater increase in emg activity during an activation of the disabled muscle than the contralateral antagonistic muscle shows during an identical contraction of the control muscle. The resting emg of the muscle antagonistic to the disabled muscle must be known since in some disabling conditions, the antagonistic muscle may be spastic, that is, abnormally high even when at rest. This is taken into account by adding the resting value to the value obtained from the contralateral antagonist muscle. Thus, the values for both antagonist muscles will be equal, and the difference will be zero, resulting in a zero intentional disability value. When, on the other hand, a disability is faked by voluntarily activating the antagonist muscle to offset concomitant activation of the "disabled" muscle, the value of $A_D$ above that of $A_C$ plus $A_DR$ should be in the neighborhood of the value for $P_C$. If this difference of $A_D$ above $A_C+A_DR$ is equal to $P_C$, then the ratio $=1$ and the intentional disability $= 100\%$. If the difference is more than normal but less than $P_C$, the intentional disability will be a proportional percentage of $P_C$, that is, a proportion of 100%.

The total quantized value for the intentional disabling of a muscle can be derived from the following equation:

$$ID = ID_S + ID_A \tag{3}$$

In performing the test, a record is made of the integrated emg of the disabled antagonist muscle while at rest. Then a simultaneous recording is made of the integrated emg of the disabled muscle, its synergist and its antagonist muscles while the patient is performing a predetermined work task. Next, the integrated emg of the control muscle, its synergist and its antagonist muscles are recorded while performing the same task. From these recordings, the aforementioned equations 1-3 are solved to arrive at a quantized level of the intentionally induced disability of a muscle.

Four examples of calculation of ID are set out below:

|   |   | I | II | III | IV |
|---|---|---|---|---|---|
| $P_C$ | = | 10,000 | 10,000 | 10,000 | 10,000 |
| $P_D$ | = | 6,000 | 6,000 | 6,000 | 6,000 |

-continued

|  | I |  | II | III | IV |
|---|---|---|---|---|---|
| $S_C$ | = | 2,000 | 2,000 | 2,000 | 2,000 |
| $S_D$ | = | 1,200 | 1,200 | 1,200 | 2,000 |
| $A_C$ | = | 300 | 300 | 300 | 300 |
| $A_D$ | = | 300 | 3,300 | 6,300 | 6,300 |
| $A_DR$ | = | 0 | 0 | 0 | 0 |
| $EmgWD_P$ | = | 40% | 40 | 40 | 40 |
| $ID_S$ | = | 40% | 40 | 40 | 0 |
| $ID_A$ | = | 0% | 30 | 60 | 60 |
| $ID$ | = | 40% | 70 | 100 | 60 |

The term $EmgWD_P$ gives a measure only of the physiological activity of work performed by the primary, i.e., "disabled," muscle; whereas the actual work performed by the subject depends also on any synergist activity and any voluntary or involuntary activity of the antagonist muscle(s) which would proportionately reduce the amount of the work which the primary muscle delivers. Thus, the following equation gives $EmgWD_P$:

$$EmgWD_P = 100 - 100(P_D/P_C) \qquad (4)$$

Since the subscript S represents degree of voluntary contraction and the subscript A represents degree of voluntary antagonism which offsets a contraction, each represents a separate and different mechanism for creating an intentional disability. Both of these effects summate and thus $ID_S$ and $ID_A$ should be added for total ID.

A second set of examples of calculation of ID is set out below:

|  | V |  | VI | VII | VIII |
|---|---|---|---|---|---|
| $P_C$ | = | 10,000 | 10,000 | 10,000 | 10,000 |
| $P_D$ | = | 6,000 | 10,000 | 4,000 | 10,000 |
| $S_C$ | = | 2,000 | 2,000 | 2,000 | 2,000 |
| $S_D$ | = | 2,000 | 2,000 | 3,000 | 2,000 |
| $A_C$ | = | 300 | 300 | 300 | 300 |
| $A_D$ | = | 6,300 | 5,300 | 300 | 100 |
| $A_DR$ | = | 6,000 | 0 | 0 | 0 |
| $EmgWD_P$ | = | 40% | 0 | 60 | 0 |
| $ID_S$ | = | 0% | 0 | −50 | 0 |
| $ID_A$ | = | 0% | 50 | 0 | −2 |
| $ID$ | = | 0% | 50 | 0 | 0 |

A positive value for $ID_A$ does not necessarilly mean that the patient is aware that he is contracting his antagonist thereby opposing the primary muscle. It does mean that the antagonism is voluntary and can be eliminated by the patient once informed, if he is cooperative. A negative value for $ID_S$ should be rendered as zero, since it merely means that the patient is trying harder with the "disabled" muscle and thus activates more of the synergist than under control conditions. A patient who tries harder in this manner cannot have a negative intentional disability beyond zero — obviously, zero is total absence of intentional disability. A negative value for $ID_A$ is of no significance since the patient cannot exert less than zero antagonism and therefore less than zero malingering. Therefore, render a negative value for $ID_A$ as equal to zero. Normal variation in $A_C$ and $A_DR$ values must be established so that one can disregard variations within the norm as insignificant in calculating $ID_S$ and $ID_A$.

It should be understood that the emg values could be recorded on a strip chart or stored in a digital computer. If recorded on a strip chart, the values can be read from the chart and substituted into equations 1 and 2 to derive the level of malingering. If the emg values are stored in a computer, one of ordinary skill could easily program the computer to solve equations 1-3 to arrive at the level of malingering. There may be other ways of recording the emg values and computing the intentional muscular disability of a patient. However, it should be understood that these and other recording and computing techniques are contemplated by applicant's invention as defined by the appended claims.

What is claimed is:

1. A method of detecting the intentional disabling of a muscle comprising the steps of:
   measuring the neuromuscular activation of a muscle which is an antagonist to said disabled muscle when preforming a predetermined work task, and when at rest,
   measuring the neuromuscular activation of a control muscle which corresponds to said antagonist muscle when performing said work task,
   measuring the neuromuscular activation of a control muscle which corresponds to said disabled muscle when performing said work task,
   comparing the neuromuscular activity of said antagonist muscles to thereby derive the difference in neuromuscular activity therebetween, and
   comparing said difference in neuromuscular activation of said antagonist muscles to said measured activation of said control muscle corresponding to said disabled muscle.

2. The method of claim 1 further comprising the steps of measuring the neuromuscular activation of a muscle which is an antagonist to said disabled muscle by measuring the integrated electromyogram thereof when said antagonist muscle performs said predetermined work task, measuring the neuromuscular activation of a control muscle corresponding to said antagonist muscle by measuring the integrated electromyogram thereof when performing said work task, measuring the neuromuscular activation of a control muscle corresponding to said disabled muscle by measuring the integrated electromyogram thereof when performing said work task, comparing the integrated electromyograms of said antagonist muscles to thereby derive the difference in neuromuscular activation of said muscles, comparing said difference in neuromuscular activation of said antagonist muscles to the integrated electromyogram of said control muscle corresponding to said disabled muscle.

3. The method of claim 2 further comprising the step of measuring the neuromuscular activation of said antagonist muscle by measuring the integrated electromyogram thereof when at rest, and solving the following equation:

$$ID_A = 100(A_D-(A_C+A_DR))/P_C$$

where $A_D$ is the integrated electromyogram of said antagonist muscle, $A_DR$ is the integrated electromyogram of said antagonist muscle when at rest, $A_C$ is the integrated electromyogram of said control muscle corresponding to said antagonist muscle and $P_C$ is the integrated electromyogram of said control muscle corresponding to said disabled muscle.

4. The method of claim 1 further comprising the steps of
   comparing the neuromuscular activation of said control muscle which corresponds to said antagonist muscle with said antagonist muscle when said disabled muscle is at rest, wherein said comparing said difference in neuromuscular activation of said antagonist muscle to said measured activation of said control muscle includes the step of comparing the difference in neuromuscular activation of said control muscle and said antagonist muscle when said disabled muscle is at rest with said measured activation of said control muscle.

5. A method of detecting the intentional disabling of a muscle comprising the steps of:
measuring the neuromuscular activation of a muscle which is synergist to said disabled muscle by recording the integrated electromyogram of said muscle when performing a predetermined work task,
measuring the neuromuscular activation of a control muscle corresponding to said synergist muscle when performing said work task by recording the integrated electromyogram of said muscle when performing said work task, and
comparing said integrated electromyograms of said synergist muscles to derive the relative activation of each muscle.

6. A method of detecting the intentional disabling of a muscle comprising the steps of:
measuring the neuromuscular activation of a muscle which is synergist to said disabled muscle by recording the integrated electromyogram of said muscle when performing a predetermined work task,
measuring the neuromuscular activation of a control muscle corresponding to said synergist muscle when performing said work task by recording the integrated electromyogram of said muscle when performing said work task, and
comparing said integrated electromyograms of said synergist muscles to derive the relative activation of each muscle by solving the following equations:

$$ID_S = 100 - 100 S_D/S_C$$

where $S_D$ is the integrated electromyogram of a muscle which is synergist to said disabled muscle and $S_C$ is the integrated electromyogram of said control muscle, and $ID_S$ is the quantized intentional disability of said disabled muscle.

* * * * *